United States Patent [19]

Doane et al.

[11] Patent Number: 5,557,036
[45] Date of Patent: Sep. 17, 1996

[54] DARK RED KIDNEY BEAN VARIETY AND METHOD OF PRODUCTION

[76] Inventors: Russell C. Doane, Rte. 3, Box 170, Menomonie, Wis. 54751; Donald Hagedorn, 927 University Bay Dr., Madison, Wis. 53705; Karl W. Young, 1400 E. 12th Ave., Menomonie, Wis. 54751; Robert E. Rand, 401 Eau Claire Ave. Apt. 119, Madison, Wis. 53705

[21] Appl. No.: 193,560

[22] Filed: Feb. 8, 1994

[51] Int. Cl.⁶ ..................................................... A01H 5/00
[52] U.S. Cl. ................. 800/200; 800/255; 800/DIG. 23; 47/58
[58] Field of Search ..................... 800/200, 205, 800/255, DIG. 23; 47/58.03, 58.05

[56] References Cited

U.S. PATENT DOCUMENTS 4,368,592  1/1983  Welch ........................... 47/58
4,705,910  11/1987  Price ............................. 800/1

OTHER PUBLICATIONS

Schwartz et al. Biological Abstracts #44469. 76(6) (1983).
Correa et al. (1987) Plant Disease vol. 71 #10 pp. 915–918.
Bliss et al. (1983) "Plant Breeding Reviews" Ed J. Janick, pp. 59, 84–87.
R. E. Rand, W. F. Pfender and D. J. Hagedorn "Resistance in Red Kidney Beans to Wisconsin's Bean Root Rot Complex, " 1983.
D. J. Hagedorn and R. E. Rand "Rate Reducing Disease Resistance in Phaseolus Vulgaris to Isariopsis Griseola", 1985.

*Primary Examiner*—Gary Benzion
*Attorney, Agent, or Firm*—Joel D. Skinner, Jr.

[57] ABSTRACT

A variety of dark red kidney beans, having the characteristics of an upright plant structure of at least 55 cm tall; a medium to large bean seed size, a bean seed total yield weight per plant of at least 45 grams; resistance to root rot disease; strong tolerance to angular leaf spot disease; superior pod suture strength; and superior canning quality.

6 Claims, 6 Drawing Sheets

DARK RED KIDNEY BEAN VARIETY AND METHOD OF PRODUCTION

BACKGROUND OF THE INVENTION

1. Field of the Invention

This invention relates to dark red kidney bean varieties and methods of production therefor and more particularly to an improved dark red kidney bean with several desired characteristics.

2. Description of the Related Art

While several commercial or former commercial varieties of dark red kidney beans are known to bean breeders today, only two of these varieties are currently in wide use commercially. All of these known varieties exhibit one or more marked weaknesses in their makeup. All are susceptible to two common and often debilitating diseases; root rot and angular leaf spot. All of them have weaknesses in commercial canning quality which is a serious flaw as almost all dark red kidney beans are commercially canned before reaching the consumers table. As a result, canner buyers in America and overseas markets have come to demand a bean that will consistently retain excellent quality throughout the canning process. Finally, all of the currently known varieties leave much to be desired in their general plant vigor and yield characteristics.

In the past several decades, virtually all dark red kidney bean breeding work has been carried on at the public universities of this country with only public funding to carry the load. As a result, the funds for such work were constrained and the goals were invariably narrowed to fit those limited budgets. The breeding projects typically concentrated on only one trait at a time, such as improved halo blight resistance, or improved heat tolerance in a variety. Almost always the improvements were derived from. crosses and/or selections from existing commercial lines of beans. No effort was made to go back to search through the much wider gene pool of wild or exotic specimens of the same genus and specie, *Phaseolus vulgaris*, with the goal of achieving major multiple trait improvements in a totally new variety.

Thus it is an objective of the present invention, through the use of back crossing and multiple recurrent selection, to provide a widely improved variety of dark red kidney bean plant, possessing superior overall plant vigor and yield, a high degree of resistance to root rot disease, a high tolerance to angular leaf spot, improved pod strength for good pre-harvest seed retention, and with seed possessing consistently superior canning characteristics, while retaining good dark red kidney been type, size, shape and color.

SUMMARY OF THE INVENTION

The present invention provides a new variety of dark red kidney beans. Preferred embodiments include 110A, 07 and 85 varieties which are produced by a back cross method followed by a recurrent selection method. The beans of all three preferred embodiments, upon growth, yield plants having the characteristics of an upright plant structure of at least approximately 55 cm tall, medium to large kidney bean type seeds, a bean seed total yield weight per plant of at least approximately 45 grams, resistance to root rot disease, tolerance to angular leaf spot disease, superior pod suture strength, and superior canning quality.

The benefits of this invention will become clear from the following description.

DESCRIPTION OF THE PREFERRED EMBODIMENTS

1. Plant Pathogens

Figure 3:
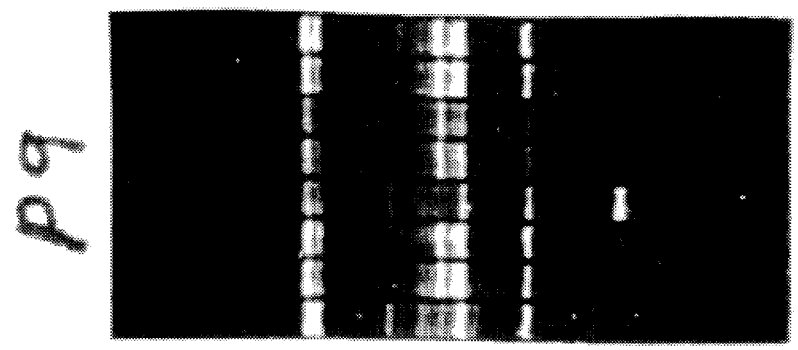
FIG. 3 shows the DNA phenotypes for RAPD Analysis for the primer P9.
Figure 2:
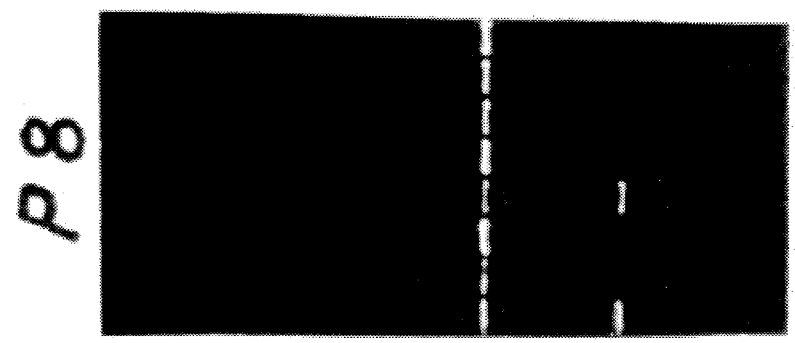
FIG. 2 shows the DNA phenotypes for RAPD Analysis for the primer P8.

Root rot disease of dark red kidney beans is caused by a complex of at least two soil fungi, Pythium sp. and *Aphanomyces euteiches* f. sp phaseoli. Several species of Pythium may be involved in the disease including *P. ultimum, P. irregulare, P. aphanidermatum* and *P. myriotylum*. The infection commonly takes place in the first two to four weeks of seedling life, after which time the plant becomes more resistant.

The effect of this disease is a progressive rotting away of the roots and hypocotyl of the young bean plant. The diseased areas are typically reddish-brown in color. Young plants are either killed before blossoming stage, or are very severely reduced in size and vigor by the disease to the point where very few, if any, blossoms or pods are formed. The result is a very severe loss of yield.

Angular leaf spot disease of dark red kidney beans is caused by a fungus, *Phaeoisariopsis griseola*, also called *Isariopsis griseola* in some scientific literature. Disease symptoms may occur on most aerial parts of the plants, but are most common on leaves, especially those on plants which are in the late flowering, early pod stage. The individual lesions are at first gray, later brown and have initially indefinite margins. Finally, the lesions fill out to have definite margins as they reach the veinal boundaries of the initial location on the leaf and become angular in shape. Under humid conditions, the under side of the lesions forms gray-black condiophores and conidia. All the leaves of heavily infected plants prematurely turn yellow and abruptly drop off the plant. This premature defoliation causes severe yield reduction if it occurs before seed maturity. Pod lesions are oval in shape, have dark brown borders, and have reddish centers. Diseased pods do not fill properly and produce shriveled seeds, thus significantly reducing quality and yield. Angular leaf spot was first discovered in Italy in 1848, and since then has been reported in many bean growing parts of the world. Angular leaf spot has the potential to seriously reduce yields in affected areas.

2. Description of Starting Material

Plant introduction (PI) 209488 was first identified and collected from the wild state in Costa Rica by Oliver Norvell in 1953. PI209488 is deposited at the U.S.D.A. Western Regional Plant Introduction Station, 59 Johnson Hall, Pullman, Wash.

A significant feature of PI209488 is it's very large fibrous root system. The hypocotyl is extremely large, and may be up to approximately one inch in diameter at the soil line. The tap root is very long and substantial. Many secondary and tertiary roots develop from the tap root. Such a large root system provides an excellent foundation, firmly anchoring the plant in the soil. The healthy root system is very efficient for providing the plant with adequate water and nutrients to promote and achieve superior plant growth both vegetatively and reproductively.

PI209488 has what is known as a "type 4a" growth habit, meaning that it is indeterminate, and continues to grow producing several (4–8) vines which extend outward from the hypocotyl. The vines may each grow from 4 to 8 feet (1.2–2.4 meters) long and every 10 to 14 inches (25.4–35.56 centimeters) a node is formed, each of which produces an upright vertical shoot which bears at least one pod.

Pods are distributed along the entire length of the plant. The pods are above average in length, and contain 5 to 7 seeds each. The very large number of pods per plant and seeds per pod result in a plant with very high yield potential. The pod sutures are very strong, a feature which enables the pod to withstand repeated wetting and drying without bursting open (a phenomenon known as "shelling") with a resulting loss of beans or loss of yield. By comparison present commercial varieties often experience yield losses due to pod shelling as high as 30 percent during infavorable conditions. In addition, the pod walls of PI209488 are thin, permitting a rapid dry down at maturity which is an advantage at harvest time.

As a result of the indeterminate nature of PI209488, the plant's reproductive growth cycle achieves maximum yield potential. The plant does not prematurely senesce resulting in shriveled seeds that reduce the quality and quantity of seed produced, as occurs in some commercial varieties.

For the most part, the leaves of PI209488 are small which is a very distinct advantage concerning white mold caused by *Sclerotinia sclerotiorum*. The smaller leaves allow for light to penetrate the plant canopy. Small leaf size also permits greater air movement thus reducing the humidity in the plant canopy that is very favorable for white mold development.

Seeds of PI209488 are small, uniformly red in color, but do not have good kidney bean shape. They tend to be "blocky" rather than kidney shape.

PI209488 has the unique ability to germinate and emerge from highly root rot infested soil without the addition of the fungicide, Captan, which is routinely applied as a seed protectant to current commercial varities. This genetic seedling protection and vigor is a very important trait which continues throughout the life of the plant.

The California Dark Red Kidney Bean (CDR) is the result of a cross between the Michigan Dark Red Kidney Bean and the Maui Red Kidney Bean made in 1948 by Francis Smith of the California Experiment Station. The Maui variety is a large, late, high producing bush type from Hawaii. California Dark Red Kidney bean plants are a bush type plant with pinkish flowers and large dark red seeds. The seed does not fade but retains its color after cooking. The California Dark Red Kidney bean has a larger, stronger plant type than Michigan Dark Red and yields equal to the Light Red Kidney variety.

Montcalm, formerly known as Michigan DRK023, is derived from the cross Great Northern No. 1 and Red Kidney. The variety was developed by Dr. M. W. Adams, a plant breeder at the Michigan Agricultural Experiment Station, and Dr. A. W. Saettler, a U.S.D.A. Plant Pathologist. Montcalm has been evaluated for agronomic performance, disease resistance, and canning quality since 1969. Montcalm is tolerant to halo blight (*Pseudomonas syringae phaseolicola*), a major seed-transmitted disease which is prevelent in the humid Great Lakes production areas. It is resistant to bean common mosaic virus (type strain and its New York variant), but susceptible to the beta strain of anthracnose (*Colletotrichum lindemuthianum*).

Montcalm is similar to the halo blight and mosaic virus susceptible Charlevoix variety in plant habit, maturity and yield. Montcalm possesses an upright bush habit and matures in approximately 90–95 days. It also has good seed quality and produces an excellent canned product. However, Montcalm remains susceptible to the seed-borne common and fuscous bacterial blights, is highly susceptible to root rot and angular leaf spot, and is subject to heavy preharvest shelling of its pods.

| PHENOTYPIC COMPARISONS | | | |
|---|---|---|---|
| Phenotypical Characteristic | CDR | PI209488 | Montcalm |
| Seed Color: | Medium Brownish-red | Bright red | Maroon-dark red |
| Seed Size: | Good | Small | Very Good |
| Seed Shape: | Good | Poor | Very Good |
| Canning: | Fair/poor | N/A | Very Good |
| Growth Habit: | Determinate Type 1/ Upright Very Good | In-determinate Type 4a | Determinate Type 1/ Upright Good |
| Roots: | Good | Excellent | Fair |
| Root Size: | Good | Excellent | Fair |
| Pythium/ Aphanomyces: | Susceptible | Resistant | Highly Susceptible |
| Angular leaf spot: | Susceptible | Tolerant | Highly Susceptible |
| Halo blight: | Susceptible | Susceptible | Resistant |
| Bean Common Mosaic Virus: | Susceptible | Resistant | Resistant |

3. Advantages and Disadvantages of the Starting Material

In general, CDR has the disadvantages of an erratic, sometimes brownish bean seed color; disease susceptibility; an ordinary root system; and it does not can (process) well. Its strength is that it has a very vigorous upright plant growth habit. Montcalm has the disadvantages of an only fair root system, a week pod suture and high susceptibility to root rot and angular leaf spot diseases. PI209488 has the disadvantages of poor seed size, shape and color and a vine type plant growth habit. Its advantages or strengths are a large, excellent root system, resistance to root rot and good tolerance to angular leaf spot, and superior yield capability.

Particular phenotypical shortcomings or limitations with respect to the CDR and Montcalm starting material are as follows:

A. CDR
 i. Bean exhibits skin weakness in canning which results in transverse rupturing of the skin.
 ii. Bean tends to be lighter and more brownish in color than is desirable in dark red kidney beans.
 iii. Plant is highly susceptible to Pythium and Aphanomyces root rots.
 iv. Angular leaf spot susceptible.

B. MONTCALM
 i. Plant is highly susceptible to Pythium and Aphanomyces root rots.
 ii. Plant lacks general vigor; is extremely floppy with large number of pods in contract with the ground. This results in increased numbers of germinated seed in the pod and/or, decayed and moisture damaged beans.
 iii. Highly susceptible to angular leaf spot; *Isariopsis griseola*.
 iv. Plant pod sutures are extremely weak; shells very readily in the field with attendant high field losses at harvest.
 v. Plant is highly determinate and therefore recovers very slowly and poorly from hail damage.
 vi. Bean tends to sprout easily in the pod at relatively low temperatures and moisture levels.
 vii. Plant does not thrive or produce well in high temperature climates.
 viii. Skin wrinkles excessively after rainy weather at maturity.

The particular strengths with respect to each starting material are as follows:

A. CDR
 i. Good seed size.
 ii. Sturdy, vigorous, upright plant structure.
 iii. Determinate plant which recovers well from hail or pest damage.

B. MONTCALM
 i. Very desirable deep red seed color.
 ii. Very desirable canning quality (i.e. the skin remains intact during the canning and cooking process with color remaining very uniformly deep red).
 iii. Very desirable seed size and shape.

C. PI209488
 i. Highly resistant to Pythium and Aphanomyces root rot pathogens.
 ii. Unusually high number of pods per plant and unusually high number of beans per pod resulting in superior yield potential.
 iii. Produces a vigorous plant with a large rugged root system superior to all current commercial varieties of dark red kidney beans.
 iv. *Isariopsis griseola* tolerance based on slow rate of lesion development.
 v. Superior pod suture strength.
 vi. Plant has indeterminate characteristics
 vii. Bean does not sprout readily in pod after maturation in presence of moisture and heat.

4. Method of Development

The dark red kidney bean varieties of the present invention are produced by techniques known in the art. In a preferred embodiment, the dark red kidney bean varieties are produced by the techniques of repeated cross-pollinations, accompanied by selection and back crossing.

PI209488 was planted at the University of Wisconsin, Hancock Experimental Farm, field W7, located in Hancock, Wis., a field that has experienced a 20 year continuous monoculture of *Phaseolus vulgaris* resulting in an intensely high concentration of root rot pathogens, in 1981 and 1982. Superior root rot resistant plants were identified and seed was harvested from these plants to be used in the breeding program. Uniformity was determined by visual examination and inspection of plants and seeds. California Dark Red and Montcalm were not selected prior to use in the breeding program. No modifications of the seeds were performed.

Field testing of all new kidney bean varieties was conducted at the University of Wisconsin Hancock Experimental Farm. The experimental design was a randomized block consisting of six replicates and treatments. Date of planting was usually mid-May. Seeds were planted six inches apart in ten foot plantings. The row spacing is 36 inches and row length is 450 ft. The soil type is Plainfield loamy sand. Before planting, 300 lbs. per acre of 6-24-24 fertilizer was applied in the row. Supplemental nitrogen, 34-0-0, was applied four weeks after planting at the rate of 100 lbs. per acre. Herbicide applications of Treflan and Eptam were applied PPI at the rate of 1½ pints per acre and 3 lbs. per acre respectively. Additional weed control was accomplished by cultivating and hand weeding. Diazinon was applied PPI at the rate of 3 lbs. per acre. The field was watered twice each week with a Water Winch 1400 traveling gun. Plants were harvested in mid-September.

Additionally, winter greenhouse challenging with the angular leaf spot pathogen, *Isariopsis griseola*, has been conducted since the winter of 1981/82. Winter greenhouse experiments was first used to screen several highly root rot resistant PI209488 selections from summer, 1981, and to evaluate the commercial varieties, CDR and Montcalm, in the winter of 1981/82. Subsequently, progensis were challenged each winter to determine that the high degree of angular leaf spot disease tolerance identified in PI209488 was carried through into the progeny.

The crossing program utilized the back cross method. Original crosses were made with PI209488 and CDR. Reciprocal crosses were also made using PI209488 and CDR. A cross was then made between the F2 of these crosses and Montcalm. Repeated back crosses were then made to Montcalm (recurrent parent) to enhance seed size, shape and color while maintaining good canning quality, plant type, pod suture strength, root rot resistance and angular leaf spot tolerance.

A first preferred variety, 110A was produced by a method utilizing the original cross of CDR X PI209488. The second cross was then made between Montcalm X male progeny of the original cross. The third cross was then made of the female progeny of the second cross X Montcalm.

A second method involved an original cross of PI209488 X CDR. The second cross involved female progeny of the first cross X Montcalm. The third cross involved the female progeny of the second cross X Montcalm. Selection of the plural individuals of this third cross yielded 85 and 07. Two other less preferred varieties 91 and 49 were also isolated.

Crosses were followed by the recurrent selection method under disease pressure to concentrate the favorable genes from the previous generation. The following is a list of the selection criteria: emergence, seedling vigor, root rot resistance, angular leaf spot tolerance, plant vigor, stem diameter, root volume, increased height, shape, pod length, pod placement, maturity, yield, seed size, shape and color.

Field observation data was compiled for approximately nine years of the project. Relative markings on a scale of one to five, or excellent, very good, good, fair, poor were used to classify these results. Detailed data on plant height in centimeters, lowest pod distance from the ground in centimeters, yield per plant in grams, and average pod weight in grams were kept. Plants were screened for the specific criteria of being at least 55 centimeters tall, having at least 45 grams seed yield per plant and all pods being off the ground.

5. Description of the End Product Variety

The three varieties, 110A, 07 and 85, were isolated from the above-described crossing and selection program. Varieties 110A and 85 are deposited at the American Type Culture Collection in Rockville, Md. USA, and have ATCC accession Nos. 97284 and 97283, respectively. These resultant red kidney bean varieties were compared with Montcalm, which is the industry standard for seed quality, plant characteristics, canning quality and yield for dark red kidney beans, with respect to the evaluation criteria listed above.

Test canning of varieties 110A, 07 and 85 has been done by canners in the U.K. and in the United States, as well as at food testing facilities of the University of Wisconsin, Madison, Wis., and Michigan State University, East Lansing, Mich. These varieties were ranked in all cases to have performed as well as or better than the Montcalm standard.

The advantages shared by the red kidney bean varieties 110A. 07 and 85 over common varieties are several. The first is that they are highly resistant to root rot caused by Aphanomyces and Pythium. Also, they have the unique ability to germinate and emerge without the benefit of the seed treatment fungicide Captan. They are also tolerant to angular leaf spot. Pods do not open readily upon wetting and drying, thereby reducing yield loss. In addition to improved yields due to loss minimization, the new bean varieties exhibit exceptional canning quality.

The resultant plants of all three varieties have the following characteristics derived from the series of crosses and repeated selections:

a) Bean seed—superior color, size, shape and canning quality.

b) Bean plant—upright plant which under some conditions produces a few short branches which produce upright pod bearing stems.

c) Bean root—very superior root system, large size, vigorous.

d) Disease reaction—resistance to root rot, tolerance to angular leaf spot, resistance to bean virus (common bean mosaic).

The strengths of the new varieties derive from the combination of each of the starting materials. Seed characteristics such as canning quality most likely derives from PI209488. Seed color and shape are likely derived from Montcalm, while seed size is derived from CDR. The plant characteristics of vigor, root system structure and yield potential are likely derived from PI209488, while upright stature is derived from CDR. Importantly, disease resistance characteristics are derived from PI209488.

The new varieties are very stable because they are advanced generations, having been self pollinated for at least seven generations. These generations have been visually examined with extreme care with each production, and all off type plants were removed. The seeds also have been visually examined for uniformity and the off types have been removed. During the production of advanced generations (F5, F6 and F7) these new varieties have proven to be very uniform. Each variety has remained unchanged for several generations of subsequent seed reproduction.

The varieties are very uniform. In the early stages of development, indeterminate plants were present, as were plants which contained seeds that were not of the proper shape, color or size. With repeated inspection and selection of plants and seeds, the new varieties are now very uniform. The numbers of variants and their frequency of occurrence is low, predictable and commercially acceptable.

The new dark red kidney bean varieties have several distinctive morphological and physiological characteristics which set them apart from all other varieties of dark red kidney beans.

a) They are highly resistant to Aphanomyces and Pythium root rot.

b) They all possess excellent seedling vigor as expressed by the fact that they will germinate, emerge and grow without the benefit of seed protectant.

c) They are the highest yielding dark red kidney bean varieties insofar as is known. All varieties have long pods; 5–6 beans per pod are not at all uncommon, coupled with the large number of pods per plant that translates into a very high yield.

d) They all display tolerance to angular leaf spot.

All of the varieties possess additional unique characteristics. The flower bud and small young blossom appear "pinkish" (due to lavender veins) but as the bloom expands and matures it turns white. The varieties have the ability to orient the leaves and pod stems in an upright manner after lodging (caused by severe wind). This feature keeps the pods away from the soil, thus reducing yield loss because of weather damage to the seed. Another outstanding feature of this breeding is its ability to "finish" very strong, meaning the ability to fill the top pods on the plant with mature, fully developed seed. Some of the commercial varieties currently available do not have this ability, thereby reducing yields. The pods of all three varieties have a very strong suture. The pod does not open easily upon repeated wetting and drying, therefore field losses due to pod shelling are greatly reduced. Pod placement is extremely good; pods are borne up off the ground and in the middle of the plant, therefore yield losses are reduced from weather damage.

The following characteristics differentiate 07, 85, and 110A from each other.

Variety 110A produces seed of a large, "barrel" shaped type. The seed size averages between 700 to 775 seeds per pound. The seed shape resembles its CDR parent, while seed color tends to be very similar to the deep mahogany red of its Montcalm parent.

Variety 85 produces somewhat smaller and lighter red seed. The shape is flatter, more like its Montcalm parent. Seed size counts average 825 to 900 seeds per pound. Its yield capability appears to be from 25–30% higher than 110A.

Variety 07 is a full sister selection of the same breeding as 85. It, therefore, is very similar to 85 except that it has a slightly darker red color than 85, more similar in color to 110A, and averages in seed size between 85 and 110A.

6. Protein and DNA Phenotype Variation Analysis in Red Kidney Bean Lines

The 110A and 85 varieties, the most preferred embodiments, are further distinguishable by chemical analysis as described below.

A. Materials and Methods Used i) Plant Material

Seed of each of the following varieties, respectively, PI209488, 85 (142), 110A, California Dark Red, Charlevoix, Montcalm, and Royal Red. Seed from each of these varieties were germinated in pots containing an artificial soil mix and grown in a greenhouse.

ii) Isozyme Analysis

Isozyme analysis was performed on extracts from young leaf tissue and imbibed seed tissue. Approximately 100 mg tissue was crushed in 0.4 ml of 50 mM Tris maleate pH 8.0 containing 20% glycerol, 10% soluble polyvinylprolidone (PVP-40), 0.5% Triton X-100, and 14 mM 2-mercaptoethanol. Horizontal starch gel electrophoresis was performed according to standard procedures. Two buffer systems were used for electrophoresis: a pH 8.1 Tris citrate/lithium borate system (Selander et al., 1971. Studies in Genetics VI. Univ. Texas Pub. 7103:49–90) and a pH 6.5 histidine gel (Cardy et al., 1980. Dept. of Statistics Mimeo Series No. 1317. North Carolina State Univ. Raliegh.). Slices from the Tris-citrate/lithium borate gel where stained for esterase (EST), ribulose bisphosphate carboxylase (RUBISCO), seed protein, formate dehydrogenase (FDH), glucose phosphate isomerase (GPI), shikimate dehydrogenase (SKDH), glutamate dehydrogenase (GDH), and mannose phosphate isomerase (MPI). Slices from the histidine gel were assayed for esterase (EST), aconitase (ACON), diaphorase (DIAP), adenylate kinase (AdK), malic enzyme (ME), and alcohol dehydrogenase (ADH). Assay solutions were mixed according to standard recipes (Wendel and Weeden, 1990. In Isozymes in Plant Biology. D. E. Soltis and P. S. Soltis (eds.) Discorides Press, Portland, Oreg., pp. 5–45.).

iii) DNA analysis

DNA was extracted from small amounts of young leaf tissue by a mini-prep procedure (see Appendix I). About 100 mg. of tissue was crushed in 1 ml liquid $N_2$. Before the tissue thawed, 1 ml of CTAB buffer containing 0.4% 2-mercaptoethanol was added and the grinding briefly continued. Approximately 0.5 ml of this aqueous slurry was poured into a 1.5 ml. Eppendorf microcentrifuge tube containing 100 ul 24:1 chloroform/octanol. The tube was briefly shaken and incubated at 65° C. for 30 min. The solution was allowed to cool to room temperature and sufficient 24:1 chloroform/octanol was added to nearly fill the tube. The mixture was shaken vigorously to form an emulsion, then centrifuged at 5° C. for 4 min (7000×g) to separate the phases. The aqueous phase was transferred to a clean microcentrifuge tube. An equal volume of cold 95% ethanol was added to precipitate the DNA which was spooled out, washed in 76% ethanol 0.2M sodium acetate for 5 min and dissolved in 100–200 ul of TE (pH 8.0). Co-precipitated RNA was eliminated by addition of 0.7 units of RNase.

For generation of RAPD fragments, the DNA solution was diluted with three volumes sterile distilled water and subjected to PCR amplification on a Coy Model 50 Temp-Cycler. Each 25 ul amplification reaction contained: 20–40 ng of plant genomic DNA, buffer (50 mM KCI, 10 mM Tris-HCI (pH 8.3), 1.5 mM $MgCl_2$, 0.001% gelatin) 100 uM of each dNTP, 2–4 uM primer, and 1U Taq DNA polymerase (Promega). The mix was overlayed with 1 or 2 drops of mineral oil. Amplification was performed for 40 cycles with the following temperature profile: 1 min at 94° C., 2 min at 35° C., 2 min at 72° C. Cycling was concluded with a final extension at 72° C. for 8 min. Reaction products were resolved by electrophoresis on gels consisting of 1% agarose, 1% Nu-Sieve agarose, and 1× TBE buffer. Gels were stained with ethidium bromide and photographed. Amplified fragments were designated using the primer ID number, and lettering from higher to lower molecular weight. Primers were synthesized at the Cornell University Biotechnolgy Institute or purchased from Genosys Biotechnologies Inc., Houston, Tex. The sequences for the 17 primers of particular interest are given in Table 1.

TABLE 1

| Sequences of primers used in RAPD analysis | |
|---|---|
| PRIMER | SEQUENCE (5' to 3') |
| T2 | TGGTGGGTCC |
| P8 | GTCCCGTTAC |
| P9 | ACGCCCTAGT |
| P13 | GGTGATGTCC |
| P98 | GAACGACGCA |
| P143 | GCCTCATACC |
| P145 | TAGCGGCTAC |
| P161 | CGGATGCCTT |
| S5 | CCGGCTCTTG |
| S12 | GCGACGCCTA |
| S16 | CGTTGGATGC |
| S19 | TACGGCTGGC |
| S20 | TGAACCGCCG |
| S22 | CGTCGTGGAA |
| S24 | GCGGCATTGT |
| S27 | AGTGGTCGCG |
| S34 | GATAGCCGAC |

B. Results Referring to Table 2, isozyme and protein analysis revealed considerable polymorphism among the red kidney beans. Seed protein phenotypes were the most variable; however resolution was relatively poor on starch gels, and no examination of the phenotypes was made using polyacrylamide gels. The esterase phenotypes also were quite variable, and one band in the EST (lith) pattern was present in both A and C phenotypes but not in the B phenotype, suggesting that it might have been transferred from PI209488 to 85 and 110A along with the root rot resistance. The presence of the band in California Dark Red Kidney should then be considered coincidental. 85 could be identified by its unique EST pattern on the histidine gel system.

TABLE 2

Isozyme phenotypes in bean lines.

| | Bean lines | | | | | | | |
|---|---|---|---|---|---|---|---|---|
| Isozyme | PI | 85 | 110A | CA Dk red | Royal red | Mont. | Charl. | Snap bean |
| EST (his) | A | C | B | A | A | D | B | ND |
| EST (lith) | A | C | C | C | B | B | B | C |
| ME | A | B | B | B | B | B | B | A |
| AdK | A | B | B | B | B | B | B | B |

TABLE 2-continued

Isozyme phenotypes in bean lines.

Bean lines

| Isozyme | PI | 85 | 110A | CA Dk red | Royal red | Mont. | Charl. | Snap bean |
|---|---|---|---|---|---|---|---|---|
| DIAP | A | B | B | B | B | B | B | A |
| GPI | A | B | A | B | B | B | B | A |
| SKDH | A | B | B | B | B | B | B | B |
| FDH | A | B | B | B | C | B | B | ND |
| Seed Prot. | A | B | B | C | D | E | F | ND |
| RUBISCO | A | B | B | B | B | B | B | A |
| ACON | A | B | A | B | B | B | B | ND |

1 Abbreviations used: CA dk red = California Dark Red Kidney; Mont. = Montcalm; Charl. — Charlevoix; ND = not determined.

Most of the other lines can be unambiguously identified by isozyme phenotype. The PI209488 was unique for a number of isozymes, and line 110A was unique in being the only line possessing the PI209488 phenotype for ACON and GPI. Royal Red displayed a unique FDH allozyme and Montcalm a unique EST phenotype on the histidine gel. California Dark Red Kidney and Charlevoix could be defined by using a combination of several isozymes.

Figure 1:
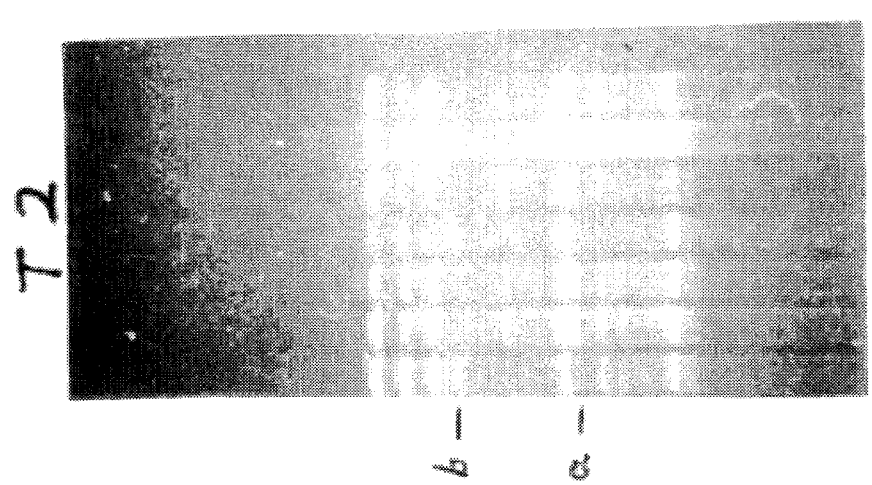
FIG. 1 shows the DNA phenotypes in bean lines PI209488, 85, 110A, California Dark Red, Royal Red, Montcalm, Charlevoix and a snap bean control (shown from left to right on electrophoresis plates) as determined by RAPD Analysis for the primer T2.
Figure 6:
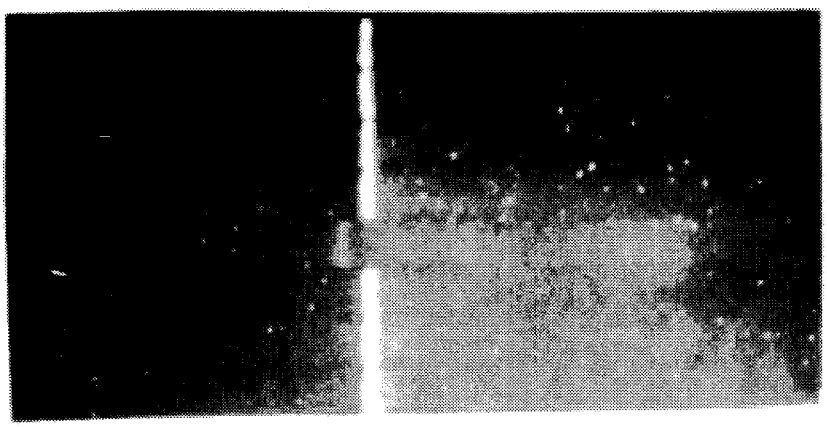
FIG. 6 shows the DNA phenotypes for RAPD Analysis for the primer P143.
Figure 5:
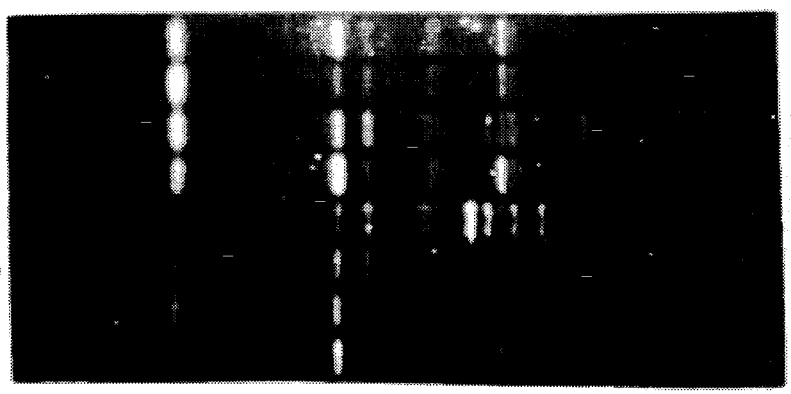
FIG. 5 shows the DNA phenotypes for RAPD Analysis for the primer P98.
Figure 4:
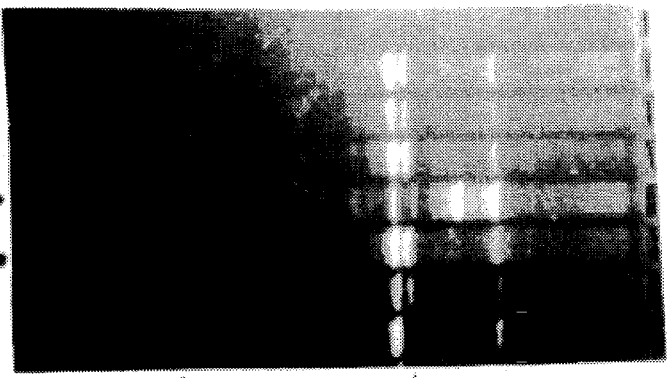
FIG. 4 shows the DNA phenotypes for RAPD Analysis for the primer P13.
Figure 9:
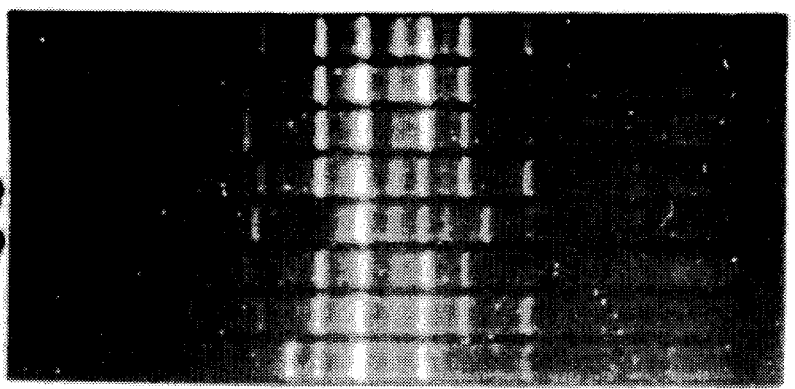
FIG. 9 shows the DNA phenotypes for RAPD Analysis for the primer S5.
Figure 8:
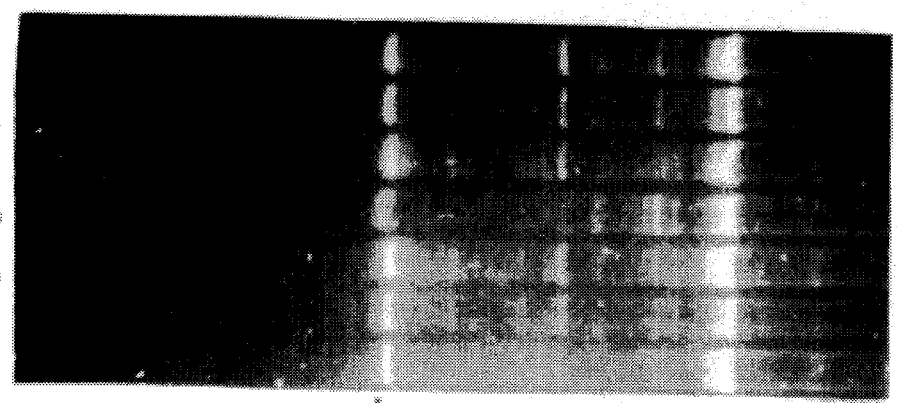
FIG. 8 shows the DNA phenotypes for RAPD Analysis for the primer P161.
Figure 7:
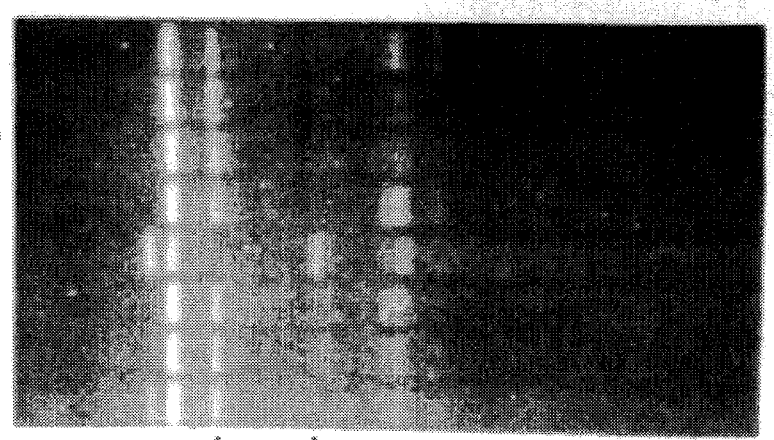
FIG. 7 shows the DNA phenotypes for RAPD Analysis for the primer P145.
Figure 12:
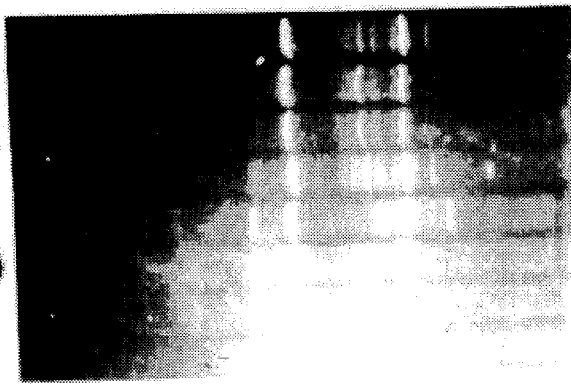
FIG. 12 shows the DNA phenotypes for RAPD Analysis for the primer S19.
Figure 11:
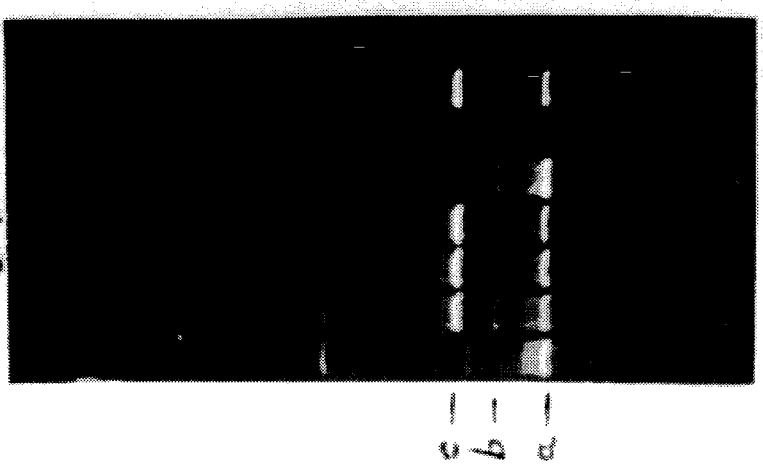
FIG. 11 shows the DNA phenotypes for RAPD Analysis for the primer S16.
Figure 10:
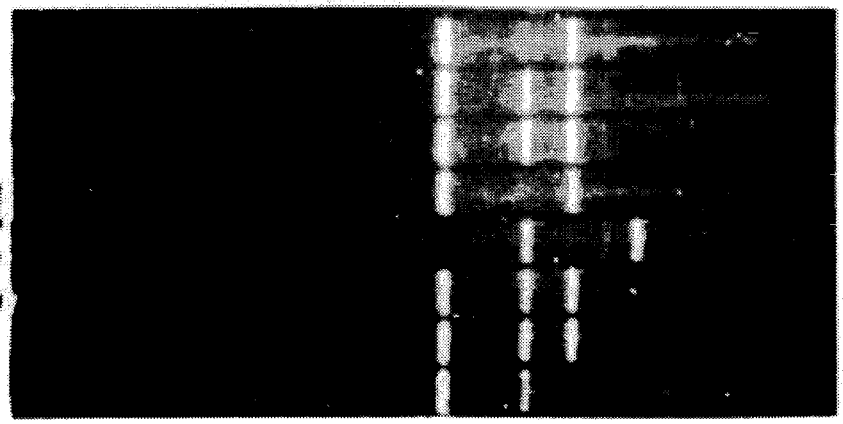
FIG. 10 shows the DNA phenotypes for RAPD Analysis for the primer S12.
Figure 15:
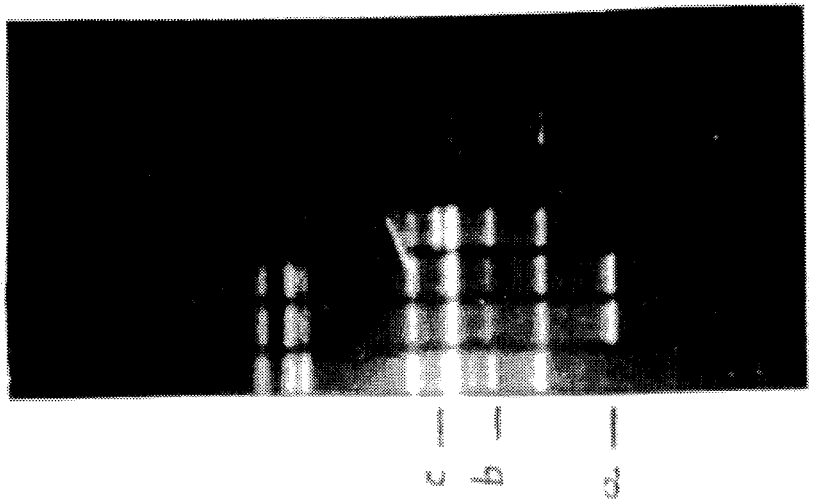
FIG. 15 shows the DNA phenotypes for RAPD Analysis for the primer S24.
Figure 14:
FIG. 14 shows the DNA phenotypes for RAPD Analysis for the primer S22.
Figure 13:
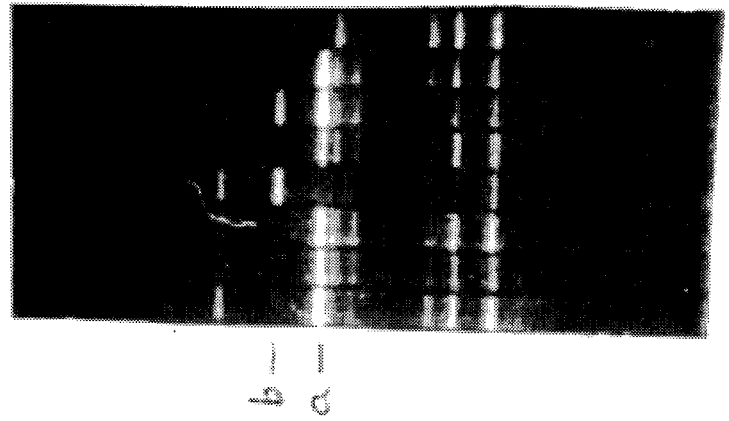
FIG. 13 shows the DNA phenotypes for RAPD Analysis for the primer S20.
Figure 17:
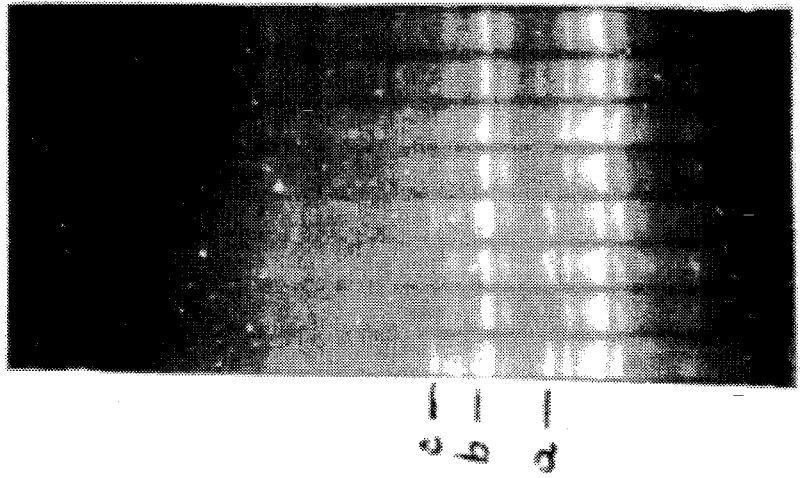
FIG. 17 shows the DNA phenotypes for RAPD Analysis for the primer S34.
Figure 16:
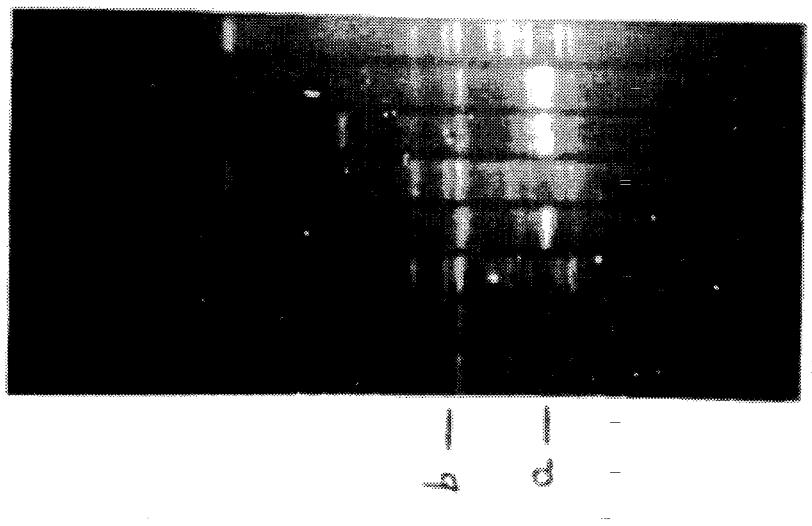
FIG. 16 shows the DNA phenotypes for RAPD Analysis for the primer S27.

The DNA phenotypes obtained for the eight bean lines are shown in FIG. 1. and the results summarized in Table 3. Again, for the DNA results PI209488 proved to be very distinctive and was more similar to a snap bean control than to any of the red kidney beans. These results indicate that the lines derived from PI209488 (85 and 110A) contain less than 10% of the genes present in PI209488. 85 appears to have retained the DNA segments from PI209488 containing the sequences P13c, P98c, and S20b. 85 also may have derived the segments for S5e, S12c, S16c, and S27a from PI209488, although these segments are found in one or more of the standard red kidney lines. Line 110A appears to have retained the DNA segments from PI209488 containing the sequence S34a, as well as perhaps S5e, S12c and S16c.

TABLE 3

DNA phenotypes in bean lines

| Primer/band | | PI | 85 | 110A | CA dk red | Royal red | Mont. | Charl. | Snap bean |
|---|---|---|---|---|---|---|---|---|---|
| T2 | a | − | + | + | + | + | + | ? | − |
|  | b | + | − | − | − | − | − | ? | + |
| P8 | a | + | − | − | − | − | − | − | + |
| P9 | pattern | A | B | B | B | B | B | B | C |
| P13 | a | + | − | − | − | − | − | − | − |
|  | b | − | + | + | + | + | + | + | − |
|  | c | − | − | + | − | + | − | − | − |
| P98 | b | + | − | − | − | − | − | − | + |
|  | c | + | +* | − | +* | − | − | − | − |
|  | d | + | − | − | − | − | − | − | +* |
| P143 | a | − | + | + | + | + | + | + | + |
|  | b | + | − | − | − | − | − | − | − |
| P145 | a | + | − | − | − | − | − | − | − |
|  | b | − | + | + | + | + | + | + | + |
|  | c | + | − | − | − | − | − | − | + |
| P161 | a | + | − | − | − | − | − | − | − |
| S5 | a | + | − | − | − | − | − | − | − |
|  | b | − | + | + | + | + | + | + | − |
|  | c | − | + | + | + | + | + | + | + |
|  | d | + | − | − | + | + | − | + | − |
|  | e | + | + | + | + | − | + | − | − |
| S12 | a | + | − | − | − | − | − | − | − |
|  | b | − | + | + | + | + | + | + | − |
|  | c | + | + | + | + | − | + | − | + |
|  | d | − | + | + | + | + | + | + | + |
|  | e | + | − | − | − | − | − | − | + |
| S16 | b | − | ? | + | + | + | + | + | − |
|  | c | + | +* | + | + | − | + | − | − |
| S19 | a | + | − | − | − | − | − | − | − |
|  | b | − | + | + | + | + | + | + | − |
| S20 | a | − | + | + | + | + | + | − | + |
|  | b | + | + | − | − | − | − | − | − |
| S22 | pattern | A | C | B | B | B | C | B | B |
| S24 | a | − | +* | + | + | ? | +* | ? | − |
|  | c | + | − | − | − | − | − | ? | − |
| S27 | a | + | + | − | − | − | + | − | − |
|  | b | − | + | + | + | + | +* | + | − |
| S34 | a | + | − | + | − | − | − | − | + |
|  | b | + | − | − | − | − | − | − | + |
|  | c | + | − | − | − | − | − | − | + |

Unique phenotypes among the red kidney beans were rare. Charlevoix was unique in lacking the S22a fragment. Charlevoix and Royal Red both lack S12c as well as S16c. Finally, Royal Red and 110A were the only lines to display the P13c fragment. However, it is possible to unambiguously identify each of the red kidney beans by their DNA fingerprints.

As many changes are possible to the embodiments of this invention utilizing the teachings thereof, the descriptions above should be interpreted in the illustrative and not the limited sense.

APPENDIX

DNA Quick Prep. for RAPD Analysis

1. Leaf (about 1 $cm^2$ of tissue frozen in liquid nitrogen) is placed in a small mortar along with 1–2 ml liquid nitrogen and gently crushed. After the liquid nitrogen has evaporated, 1 ml of CTAB extraction buffer (with 0.4% mercaptoethanol) is added and the fine leaf material further ground to form a slurry. (20–100 mM sodium bisulfate can be added just before use if material is high in phenolics).

2. Pour the slurry (leaving larger solid matter in the crucible if possible ) into an Eppendorf microcentrifuge tube containing 100 ul chloroform/octanol (24:1). Heat the tube for 20–30 min. at 65° C.

3. Cool tube and contents to room temperature and add chloroform/octanol to almost fill the tube. Shake vigorously to form and emulsion.

4. Centrifuge to separate phases and transfer aqueous (upper) phase to a clean microcentrifuge tube. There should be 0.5–0.8 ml of aqueous phase at this point.

5. Precipitate DNA by adding 0.8–1.0 ml of ice cold 95% ethanol. Layer the ethanol on top of the aqueous phase and allow to sit for 10–20 min. in order to obtain a small amount of DNA precipitate at the interphase before gently mixing the two phases.

6. Spool out DNA on a glass hook and transfer to a tube containing 1 ml of 0.2M sodium acetate in 76% ethanol. Allow to sit for 10 min.

7. Remove DNA form the ethanol/acetate solution and blot as much of the solution from the DNA as possible by repeatedly touching the DNA to the inner wall of the tube.

8. Dissolve DNA in an appropriate volume (100–200 ul) of TE (pH 8.0).

9. Store at −20° C. Preparation is stable at room temperature for at least several days.

That which is claimed is:

1. A dark red kidney bean seed variety 85 having ATCC accession No. 97284.

2. A dark red kidney bean plant produced by the seed of claim 1.

3. A red kidney bean seed capable of producing a plant having the physiological and morphological characteristics of the plant produced by variety 85 having ATCC accession No. 97284.

4. A dark red kidney bean seed variety 110A having ATCC accession No. 97283.

5. A dark red kidney bean plant produced by the seed of claim 4.

6. A red kidney bean seed capable of producing a plant having the physiological and morphological characteristics of the plant produced by variety 110A having ATCC accession No. 97283.

* * * * *